United States Patent [19]

Clark, III

[11] Patent Number: 5,028,339

[45] Date of Patent: * Jul. 2, 1991

[54] POLYMER MATRIX AND METHOD FOR RETAINING REACTANTS IN A POLYMER MATRIX

[76] Inventor: William T. Clark, III, 13 Park La., Folsom, La. 70436

[*] Notice: The portion of the term of this patent subsequent to Sep. 25, 2007 has been disclaimed.

[21] Appl. No.: 478,159

[22] Filed: Feb. 9, 1990

Related U.S. Application Data

[63] Continuation-in-part of Ser. No. 299,446, Jan. 23, 1989, Pat. No. 4,959,148.

[51] Int. Cl.$^5$ .............................................. B01D 15/08
[52] U.S. Cl. ................................... 210/688; 210/660; 210/692; 435/182; 502/402
[58] Field of Search ............... 210/635, 645, 656, 688, 210/198.2, 502.1, 506, 912, 660, 692; 525/54.1, 329.7; 435/182, 288; 422/129, 131, 239; 502/402

[56] References Cited

U.S. PATENT DOCUMENTS

| | | | |
|---|---|---|---|
| 3,859,169 | 1/1975 | O'Driscoll et al. | 435/182 |
| 4,048,064 | 9/1977 | Clark, III | 210/638 |
| 4,452,892 | 6/1984 | Rosevear | 435/182 |
| 4,452,918 | 6/1984 | Uchida et al. | 210/656 |
| 4,634,672 | 1/1987 | Baumgarten et al. | 435/182 |
| 4,855,353 | 8/1989 | Kurami et al. | 525/54.1 |
| 4,959,148 | 9/1990 | Clark, III | 210/635 |

*Primary Examiner*—W. Gary Jones
*Attorney, Agent, or Firm*—Berman, Aisenberg & Platt

[57] ABSTRACT

A method for holding a reactant in a polymer includes combining reactant, hydrogel monomer and a quenching surrogate in a solvent, whereby the solvation of the reactant and the monomer is reduced. The monomer is then polymerized to form a polymer matrix formed around the reactant with sufficient intimacy to replicate the molecular shape of the reactant without chemically attaching to or embedding the reactant. The reactant remains accessible for reaction. More than one reactant may be retained by a polymer matrix. The polymer matrix retaining the reactant is also described. The polymer matrix may be sorbed on a substrate, coated on a substrate, cast into shapes or otherwise made available for reaction.

16 Claims, No Drawings

POLYMER MATRIX AND METHOD FOR RETAINING REACTANTS IN A POLYMER MATRIX

RELATED APPLICATION

This application is a continuation-in-part of Ser. No. 299,446, filed Jan. 23, 1989, now U.S. Pat. No. 4,959,148, which is incorporated herein, by reference, in its entirety.

FIELD OF THE INVENTION

This invention relates to a polymer matrix and a method for retaining a reactant accessibly for reaction in a polymer matrix, without embedding or chemically attaching the reactant in the polymer.

BACKGROUND OF THE INVENTION

Previously known methods for retaining a reactant in a polymer have required embedment or chemical attachment of the reactant to the polymer. Such methods are described in U.S. Pat. Nos. 3,859,169; 4,855,353; 4,634,672; 4,452,892 and 4,452,918. None of these patents describes a method for retaining the molecule in condition such that it is accessible for reaction, without embedding or chemically attaching it in the polymer matrix.

In these prior art processes in which the reactant molecule is embedded in the polymer, the interstices of the polymer are smaller in size than the reactant molecule and the reactant is entrapped by the polymer matrix. Where the reactant is chemically attached to the polymer, the chemistry of the reactant is changed. In both cases the reactant is inhibited from freely reacting due to either the embedment or chemical attachment.

SUMMARY OF THE INVENTION

A polymer matrix of the invention is a hydrogel polymer which forms around a reactant and replicates the molecular shape of the reactant, and thus retains the reactant without chemically attaching, embedding or entrapping the reactant. A plurality of reactants may be retained in a single polymer matrix, and/or the polymer matrix may be based on one or more hydrogel monomers.

A method of the invention for retaining a reactant in a polymer includes combining reactant, hydrogel monomer and a quenching surrogate in a solvent, whereby the solvation of the reactant and the monomer is reduced. The monomer is then polymerized to form a polymer matrix around the reactant with sufficient intimacy to replicate the molecular shape of the reactant, thus retaining the reactant without chemically attaching or embedding the reactant. A method of the invention includes retaining more than one reactant in a polymer matrix by combining the plurality of reactants with the quenching surrogate and monomer in a solvent before polymerization.

Non-limiting examples of applications of this technology include batteries, fuel cells, photographic film emulsions, separation processes, reprographic processes and many other uses.

DETAILED DESCRIPTION OF THE INVENTION

The invention is a polymer gel which holds one or more reactant molecules by dispersion force affinity. Even though the molecular size of the reactant may be smaller than the intersticial size of the polymer, the reactant molecule is retained by the polymer matrix which forms around the reactant. The reactant molecule is not chemically attached to or embedded in the polymer, but is specifically held available for a desired localized reaction.

Moreover, if desired, the reactant molecule can be removed from the matrix without disturbing the shape of the matrix, leaving phantom shapes of the reactant molecule in the matrix. The phantom shapes of this matrix are then available to selectively retain target reactant molecules of the same shape when those molecules are presented as solutes in a fluid contacting the phantom shapes in the polymer.

Reactant molecules, which may be organic or inorganic molecules, are suitably retained for reaction by a porous hydrogel polymer matrix, without being embedded in or chemically attached to the polymer. A method for making the polymer matrix includes reversibly reducing the reactant propensity of the reactant molecules by using a displaceable surrogate compound in a solvent. This allows the polymer to form around, but not embed or chemically attach to, the reactant molecule.

A mixture containing a hydrogel monomer, reactant, and quenching surrogate is polymerized to form an insoluble crosslinked hydrogel polymer which replicates the shape of the reactant molecule and retains the molecule without embedding or reacting with it. The shaped polymer exhibits profound dispersion-force affinity for the reactant and the polymer retains the reactant located accessibly for reaction.

The quenching surrogate temporarily conceals the reactive character of the reactant until the polymer is formed. The reactant is thus "quenched" because reaction between reactant and monomer is prevented by the quenching surrogate which takes the place of both the monomer and the reactant in the solution relative to the solvent. The surrogate occupies the solvent and thereby has the effect of making both the reactant and the monomer relatively less soluble, and thus less reactive.

Since reaction between the reactant and the monomer is prevented and the relative solvations of the reactant and the monomer are altered, the surrogate also serves to prevent embedding of the reactant in the polymer, which would render it useless.

The polymer may have larger or smaller interstices than the size of the reactant molecule. Even though the polymer may have larger molecular interstices than the size of the reactant molecule, the reactant is intimately held in the polymer structure, without being washed out, and is available for reaction with solutes passed through a chamber containing the polymer. Alternatively, the polymer and retained reactant may be sorbed onto a substrate, coated on a substrate, cast into shapes or otherwise made available for effecting a desirable localized chemical reaction in which the retained molecule is available for reaction with another proximal reactant.

The reactant is rendered accessible with full activity, unencumbered by steric hindrance from polymer embedment, entrapment or undesirable reaction with functional groups. If desired, the reactant may be extracted from the polymer, leaving phantom shapes in the polymer matrix gel where the reactant was formerly positioned. The gel of phantom shapes of the reactant then becomes a specific sorbent for the reactant which may be removed from another situation and located in the phantom shapes in the gel. The gel having phantom reactant shaped spaces has enhanced activity for sorbing the reactant. The enhanced affinity gel may also be used in combination with, or coated over, conventional solid adsorbents and substrates, such as activated carbon or reticulated foam.

Regardless of the application, the gel must replicate the shape of the reactant molecule and retain it while remaining porous. Porosity of the hydrogel is determined by the amount of water or other polymer nonsolvent present as the gel network is formed. If the water content is too high, the resulting gel will have poor mechanical properties or will not form at all. Conversely, if the water content is too low, the gel will be insufficiently porous. The best replicating gels generally contain between about 20% and 80% by weight of water. Generally about 40% to 60% by weight of water is preferred.

Reactants suitable for use with this method include any reactant capable of effecting the desired reaction and distinguishable by shape. Reactants may be organic or inorganic molecules. More than one reactant may be retained in the hydrogel polymer.

Hydrogel polymers suitable for use with the method of this invention may be any of a wide variety characterized by inertness in the environment and having a porosity, hydraulic permeability, and other diffusion characteristics which can be predictably adjusted to allow access to the reactant. The polymer matrix is preferably crosslinked and may be formed from one or more monomers. If more than one monomer is used, the monomers are mixed before polymerizing. Suitable hydrogels include, for example, the poly(alkyl)methacrylates, polyacrylamides and their homologs and derivatives. Poly(hydroxy)ethylmethacrylate is a preferred polymer.

The quenching surrogate is selected according to its ability to quench or prevent reaction of the reactant with the hydrogel during polymerization and according to its ability to affect solvation. The quenching surrogate is further characterized by its ability to be displaced or extracted from the reactant solution after polymerization is completed, in order to allow the target reaction. The quenching surrogate, of course, should not be reactive when displaced. Suitable quenching surrogates may include such substances as, for example, ions or pseudofunctional moieties displaceable in solution. For most reactants and quenching surrogates, an approximate ratio of 1:1 is preferred, although the exact ratio may vary widely for different substances.

The concentration of an electrolytic quenching surrogate should probably not ordinarily constitute more than about 5% of the water content of the monomer-water mix or the phases will tend to separate at between 5% and 10% concentration. On the other hand, as the concentration of quenching surrogate approaches 0.2% or less, polymerization will not occur or the reactant will be rendered inactive for the target reaction.

It will be apparent to those skilled in the art that the novel shape replication polymerization principles of the present invention may be diversely applied whenever it is desired to efficaciously retain a substance species for localized reaction. It is simply necessary to adjust the relative solvation of the solution components by means of the quenching surrogate in order to polymerize the monomer in the presence of a wide variety of reactants, which reactants are then retained in the polymer matrix.

The permeable hydrogel polymer thus formed allows ready fluid communication with the retained substance which could not otherwise be usefully retained in situ for it would either inhibit monomer conversion or become useless by embedment in the polymer mass. Likewise, diverse applications for removing a substance species from an undesirable location, such as where such a substance is causing contamination, is now available using phantom shapes in a polymer, as described. This supramolecular retention technology enables unique approaches to chemical processes which were previously impossible.

In a non-limiting example, hydroquinones (and related substances such as p-methoxyphenols) are universally used as very powerful polymerization inhibitors, and they must be removed or entered into side reactions before monomer to polymer conversion is possible. Hydroquinone is also universally used as a powerful antioxidant and reducing agent in solution developers for halide process photographic systems. There is no conventional technology which enables this valuable substance to be conveniently used for localized reaction.

With the new principle of the present invention, however, the monomer can be converted to hydrogel polymer in the presence of hydroquinone, retaining the hydroquinone in the gel, while making it available for subsequent reaction with, for example, silver halides or diazonium salts also incorporated into the polymer during polymerization. If hydrogel polymer incorporating both silver halide and hydroquinone is cast in sheet form, a self-developing light sensitive film is made, of course, many variations are possible with additional incorporated reactants to influence subsequent reactions, such as color coupling. If diazonium compounds are used instead of silver salts, then the hydroquinone acts as a dye coupler, and it will be found that the proximal combination is more light-sensitive than conventional methods. Diazonium compounds, unlike hydroquinone, have the unusual property of accelerating, rather than inhibiting, polymerization ordinarily leading to useless embedment. This detrimental effect is prevented by the quenching surrogate principle described herein.

Of course, hydroquinone is not essential for all photo processes, and many other light and actinic radiation sensitive salts can be retained by this method. If a chelating agent is incorporated, then its presence will allow photosensitive dyes to reduce metal ions, often with increased sensitivity if the hydrogel also contains an humectant. Thus very sensitive specific spectral recording actinometers may be made which, if in sheet form, can record an image as well as providing a linear record of the energy exposure dose required to produce the image.

Similarly, all manner of metal salts, reactants, and other substances may be retained by the method of this invention. The essential characteristic is that a hydrogel polymer formed in the presence of a particular substance retains a specific affinity for that substance by dispersion force affinity for the replicated shape. This extreme specificity as well as the easily controlled hydraulic permeability of the hydrogel means that movement and communication through the polymer is very rapid.

This rapid specificity has great value in many electrochemical, separation, and analytical processes.

In another non-limiting example, separation electrodialysis may be conducted through these specific affinity hydrogels. It has already been shown, in Example 4 of the parent application, that energy may be applied to the hydrogel in order to remove the substance retained by the polymer. The specific affinity hydrogel remaining may then be used to separate or discriminate between substances on the basis of the phantom molecular shapes of the molecules removed from the polymer matrix, rather than using size alone, as an energy field gradient (electrical, for example) is placed across the hydrogel. A diverse array of separation, purification, and analytical processes and extractions may thus be conducted by this novel means.

In like manner, a specific affinity hydrogel may be used to retain renewable fuels and catalysts in primary and secondary batteries and fuel cells for electrochemical generation of electricity. In this application, specific reactants (complex metal salts, for example) may be easily retained proximal to the appropriate inert electrode with an inert electrolyte communicative between them, all to be in the form of sequenced layers of specific affinity hydrogels creating an electrochemical cell or battery with very low internal resistance. By virtue of localized reaction, such a cell or battery can be quickly regenerated. Highly corrosive compounds, such as dichromates, may be used in batteries of this kind when "quenched" with a surrogate according to this invention and held accessibly in a hydrogel polymer.

When bioreactants and enzymes (zymase, for example) are retained, then the current is generated by differential action at the electrodes using renewable fuel (glucose, for example), the spent fuel producing alcohol.

While the invention has been described herein with respect to certain embodiments thereof, it will be appreciated that variations and modifications may be made without departing from the spirit and scope of the invention.

What is claimed is:

1. A polymer matrix comprising a hydrogel polymer and a reactant retained by the polymer, wherein the hydrogel polymer is formed around reactant molecules with sufficient intimacy to replicate the molecular shape of the reactant, to retain the reactant without chemically attaching to or embedding the reactant.

2. A polymer matrix according to claim 1 wherein the formed polymer exhibits profound dispersion-force affinity for the reactant and the polymer retains the reactant.

3. A polymer matrix according to claim 2 wherein the polymer is crosslinked.

4. A polymer matrix according to claim 3 wherein the polymer contains about 20% to 80% by weight of water.

5. A polymer matrix according to claim 1 wherein the size of the interstices of the polymer matrix is larger than the molecular size of the reactant.

6. A polymer matrix according to claim 1 wherein the size of the interstices of the polymer matrix is smaller than the molecular size of the reactant.

7. A polymer matrix according to claim 1 wherein the hydrogel polymer comprises a polymer formed by a plurality of different monomers.

8. A polymer matrix according to claim 1 wherein the reactant comprises a plurality of different reactants.

9. A polymer matrix comprising hydrogel polymer wherein the hydrogel polymer replicates the shape of reactant molecules, said reactant molecules then being removed to leave behind phantom shapes which are able to retain reactant molecules of the same shape when said reactant molecules are solutes in a fluid which contacts the phantom shapes in the hydrogel polymer.

10. A method of retaining a reactant in a polymer matrix comprising:
    combining a reactant, hydrogel monomer and a quenching surrogate in a solvent whereby the solvation of the reactant and the monomer is reduced; and
    polymerizing the monomer to form a polymer matrix formed around molecules of said reactant with sufficient intimacy to replicate the molecular shape of the reactant, to retain the reactant without chemically attaching to or embedding the reactant.

11. A method according to claim 10 wherein the polymer contains about 20% to 80% by weight of water.

12. A method according to claim 11 further comprising crosslinking the polymer.

13. A method according to claim 10 further comprising removing reactant molecules from the polymer matrix whereby the polymer matrix retains phantom shapes of said reactant molecules.

14. A method according to claim 13 further comprising:
    contacting the polymer matrix retaining phantom shapes with reactant molecules of the same shape as the removed reactant molecules; and
    retaining said reactant molecules contacted with the polymer matrix in said phantom shapes.

15. A method according to claim 13 further comprising:
    separating molecules by providing a polymer matrix with phantom shapes of a target molecule;
    transporting a mixture of different types of molecules through the polymer matrix; and
    retaining the target molecule in said phantom shapes.

16. A method according to claim 10 comprising retaining a plurality of different reactants in the polymer matrix.

* * * * *